US012678637B2

(12) United States Patent
Rancilio

(10) Patent No.: US 12,678,637 B2
(45) Date of Patent: Jul. 14, 2026

(54) RIGIDLY INDEXED APPARATUS FOR EXTERNAL BEAM RADIOTHERAPY POSITIONING OF SMALL ANIMALS

(71) Applicant: Iowa State University Research Foundation, Inc., Ames, IA (US)

(72) Inventor: Nicholas Jacob Rancilio, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 274 days.

(21) Appl. No.: 18/661,877

(22) Filed: May 13, 2024

(65) Prior Publication Data

US 2024/0374929 A1      Nov. 14, 2024

Related U.S. Application Data

(60) Provisional application No. 63/501,749, filed on May 12, 2023.

(51) Int. Cl.
A61N 5/10            (2006.01)

(52) U.S. Cl.
CPC ......... A61N 5/1049 (2013.01); A61N 5/1071 (2013.01); *A61N 2005/1097* (2013.01)

(58) Field of Classification Search
CPC ..... A01N 5/1071; A01N 5/1049; A01G 15/04
See application file for complete search history.

(56) References Cited

U.S. PATENT DOCUMENTS

| | | | | |
|---|---|---|---|---|
| 6,143,003 A | * | 11/2000 | Cosman ................. | A61B 90/16 |
| | | | | 128/846 |
| 2020/0376297 A1 | * | 12/2020 | Anand ................... | A61B 90/16 |
| 2023/0105772 A1 | * | 4/2023 | Hoerning ............... | A01K 15/04 |
| | | | | 119/601 |

FOREIGN PATENT DOCUMENTS

| | | | | | |
|---|---|---|---|---|---|
| CN | 115397509 A | * | 11/2022 | ........... | A61N 5/1081 |
| CN | 120202959 A | * | 6/2025 | ............ | A01K 29/00 |

OTHER PUBLICATIONS

Yoshikawa et al., "Repeatability of a planning target vol. expansion protocol for radiation therapy of regional lymph nodes in canine and feline patients with head tumors," Veterinary Radiology & Ultrasound, Nov. 2012, vol. 53, No. 6, pp. 667-672.

* cited by examiner

*Primary Examiner* — Monica L Perry
(74) *Attorney, Agent, or Firm* — McKee, Voorhees & Sease, PLC

(57) ABSTRACT
To aid in the positioning of animals, such as cats and dogs, during radiotherapy treatment, a device can be indexed on a standard U-Frame. The device includes indexing holes that align with pins of the U-Frame. Based on the size of the animal, the indexing pins can be placed so the portions of the animal (e.g., head or neck) under treatment receive the radiotherapy directly. The device keeps the mouth of the animal open in a manner to further locate the animal and to aid in placement of breathing apparatus for the animal under anesthesia. The device can be sized for different sizes of animals and can also include features such as dosing meters to mitigate over treatment of the radiation used for the treatment.

20 Claims, 12 Drawing Sheets

RIGIDLY INDEXED APPARATUS FOR EXTERNAL BEAM RADIOTHERAPY POSITIONING OF SMALL ANIMALS

CROSS REFERENCE TO RELATED APPLICATIONS

This application claims priority under 35 U.S.C. § 119 to provisional patent application U.S. Ser. No. 63/501,749, filed May 12, 2023. The provisional patent application is herein incorporated by reference in its entirety, including without limitation, the specification, claims, and abstract, as well as any figures, tables, appendices, or drawings.

TECHNICAL FIELD

The present disclosure relates generally to an apparatus and/or corresponding method of use having applications in at least the veterinary industry. More particularly, but not exclusively, the disclosure relates to an apparatus, device, and/or method used to aid in positioning an animal during external beam radiotherapy.

BACKGROUND

The background description provided herein gives context for the present disclosure. Work of the presently named inventors, as well as aspects of the description that may not otherwise qualify as prior art at the time of filing, are neither expressly nor impliedly admitted as prior art.

Dogs and cats are commonly affected with head and neck cancers such as brain tumors and nasal tumors which are treated with external beam radiotherapy. Positioning devices are necessary to immobilize the head and neck for reproducible radiotherapy treatments and computed tomography simulation.

Current positioning devices come in different sizes to account for different animal sizes. The patient (e.g., cat or dog) is placed on a table under anesthesia. A portion of the animal's upper jaw (maxilla) is placed on a portion of the positioning device. The animal's teeth may be positioned on a front portion to help position the animal. The positioning device keeps the mouth of the animal in an open position, such that breathing apparatuses or the like can be inserted to help the animal breathe during the procedure. A thermoplastic mask may also be placed over the animal's head to further hold the animal in place.

The animal is then treated with the radiotherapy, such as external beam radiotherapy, in order to target and treat cancer.

However, current positioning devices are limiting. For example, most radiotherapy couches include indexing pins and measuring indicia. The pins and indicia are used to reproducibly position the patient on the radiotherapy couch to best receive the treatment. Current commercially available U-Frame apparatus are designed for human head and neck positioning. Current veterinary positioning devices are not able to be held in place once the correct positioning has been identified. This could affect the treatment, as the radiotherapy may not interact with the cancerous portions of the animal due to inaccurate daily positioning.

In addition, there could be instances of overdosing or underdosing the radiation for animals of various sizes if positioning for external beam radiotherapy is not accurate and reproducible. For example, if the radiotherapy beam misses the tumor due to positioning errors the patient's cancer would continue to grow resulting in treatment failure.

Additionally, if the high dose of radiation is aimed at the wrong place in the head and neck radiation could be harmful to the patient's normal tissues resulting in radiation side effects which may not be reversible. In the head and neck inaccurate positioning of the patient could result in the formation of ulcerations and or fistula (abnormal communication) between the nose and mouth.

Thus, there exists a need in the art for an apparatus which improves on or accounts for the limitations of current positioning devices used for radiotherapy/radiation treatment of animals, such as dogs and cats.

SUMMARY

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present disclosure to improve on or overcome the deficiencies in the art.

It is a further object, feature, and/or advantage of any of the aspects of any of the embodiments to aid in positioning an animal on a positioning device for treatment, such as radiotherapy (i.e., radiation) treatment.

It is still yet a further object, feature, and/or advantage of any of the aspects of any of the embodiments to provide varying sizes of devices to accommodate different sizes and/or breeds of animals undergoing treatment.

It is yet another object, feature, and/or advantage of any of the aspects of any of the embodiments to immobilize the head and neck of an animal for reproducible radiotherapy treatments and computed tomography simulation.

It is still another object, feature, and/or advantage of any of the aspects of any of the embodiments to include a dosimeter in or on a portion of an indexing device to measure the amount of radiation used during treatment.

The apparatus disclosed herein can be used in a wide variety of applications. For example, while radiation treatment and computed tomography simulation are referenced, generally any treatment where immobilization of an animal is needed could include aspects of the disclosure.

It is preferred that the apparatus be safe, cost effective, and durable.

The device can be used with a number of standard human positioning aids, such as a head and neck U-Frame that is commercially available, making the device generally universal in use. This includes additional features, such as commercially available thermoplastic materials used to hold a patient's head and neck during the treatment.

At least one embodiment disclosed herein comprises a distinct aesthetic appearance. Ornamental aspects included in such an embodiment can help capture a consumer's attention and/or identify a source of origin of a product being sold. Said ornamental aspects will not impede functionality of the apparatus.

Methods can be practiced which facilitate use, manufacture, assembly, maintenance, and repair of an apparatus which accomplish some or all of the previously stated objectives.

The apparatus can be incorporated into systems or kits which accomplish some or all of the previously stated objectives.

According to some aspects of the present disclosure, a device for use in radiotherapy treatment of animals comprises a raised platform; first and second feet extending substantially transverse to the raised platform; wherein the first and second feet each include at least one indexing aperture that is used to align the device during the radiotherapy treatment, said indexing apertures extending through the feet.

According to at least some aspects of some embodiments, the device further comprises an epoxy on the raised platform that is configured to be moldable to an upper jaw portion of the animal undergoing radiotherapy treatment.

According to at least some aspects of some embodiments, an indexing aperture on the first foot is positioned at the same lateral position as an indexing aperture on the second foot.

According to at least some aspects of some embodiments, an indexing aperture on the first foot and an indexing aperture on the second foot are distanced the same distance from the raised platform.

According to at least some aspects of some embodiments, the raised platform comprises a rectangular-shape with support legs extending downward from the rectangular-shaped platform.

According to at least some aspects of some embodiments, the first and second feet extend away from the support legs of the raised platform.

According to at least some aspects of some embodiments, the device further comprises a dosimeter positioned at the raised platform.

According to at least some aspects of some embodiments, the dosimeter is positioned in a plug in the raised platform.

According to at least some aspects of some embodiments, the plug is positioned at a front face of the raised platform.

According to additional aspects of the disclosure, an assembly comprises a radiotherapy positioning frame comprising a surface and a plurality of indexing tabs extending generally upward from the surface; and a radiotherapy positioning device comprising a raised platform and first and second feet extending substantially transverse to the raised platform, wherein the first and second feet each include at least one indexing aperture that is used to align the radiotherapy device relative to the radiotherapy positioning frame via engagement between the indexing tabs and the indexing apertures.

According to at least some aspects of some embodiments, the assembly further comprises a thermoplastic material operatively engageable with the frame and/or device to hold an animal in place during radiotherapy treatment.

According to at least some aspects of some embodiments, an indexing aperture on the first foot is positioned at the same lateral position as an indexing aperture on the second foot.

According to at least some aspects of some embodiments, an indexing aperture on the first foot and an indexing aperture on the second foot are distanced the same distance from the raised platform.

According to at least some aspects of some embodiments, the raised platform comprises a rectangular-shape with support legs extending downward from the rectangular-shaped platform.

According to at least some aspects of some embodiments, the first and second feet extend away from the support legs of the raised platform.

According to at least some aspects of some embodiments, the assembly further comprises a dosimeter positioned at the raised platform.

According to at least some aspects of some embodiments, the dosimeter is positioned in a plug in the raised platform.

According to additional aspects of the disclosure, a device for use in radiotherapy treatment of animals comprises a raised platform; first and second feet extending substantially transverse to the raised platform; wherein the first and second feet each include at least one indexing aperture that is used to align the device during the radiotherapy treatment, said indexing apertures extending through the feet; wherein the raised platform comprises a rectangular-shape with support legs extending downward from the rectangular-shaped platform.

According to at least some aspects of some embodiments, the first and second feet extend away from the support legs of the raised platform.

According to at least some aspects of some embodiments, the device further comprises a dosimeter positioned at the raised platform.

These and/or other objects, features, advantages, aspects, and/or embodiments will become apparent to those skilled in the art after reviewing the following brief and detailed descriptions of the drawings. The present disclosure encompasses (a) combinations of disclosed aspects and/or embodiments and/or (b) reasonable modifications not shown or described.

BRIEF DESCRIPTION OF THE DRAWINGS

Several embodiments in which the present disclosure can be practiced are illustrated and described in detail, wherein like reference characters represent like components throughout the several views. The drawings are presented for exemplary purposes and may not be to scale unless otherwise indicated.

Figure 1:
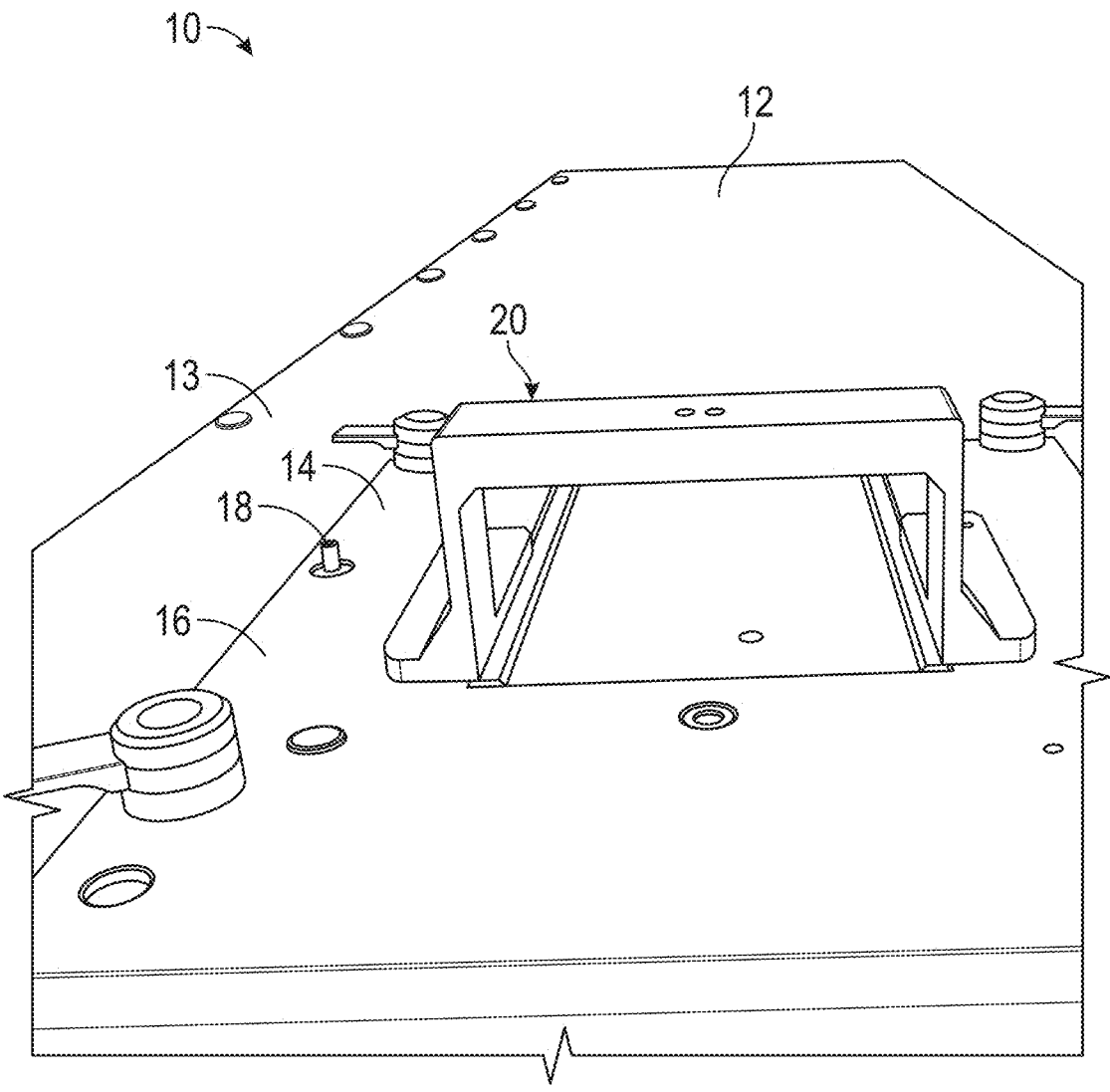
FIG. 1 is a view of a system used for radiotherapy treatment of small animals, such as dogs and cats.

An artisan of ordinary skill in the art need not view, within isolated figure(s), the near infinite distinct combinations of features described in the following detailed description to facilitate an understanding of the present disclosure.

DETAILED DESCRIPTION

Unless defined otherwise, all technical and scientific terms used above have the same meaning as commonly understood by one of ordinary skill in the art to which embodiments of the present disclosure pertain.

The terms "a," "an," and "the" include both singular and plural referents.

The term "or" is synonymous with "and/or" and means any one member or combination of members of a particular list.

As used herein, the term "exemplary" refers to an example, an instance, or an illustration, and does not indicate a most preferred embodiment unless otherwise stated.

The term "about" as used herein refers to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variables, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The "scope" of the present disclosure is defined by the appended claims, along with the full scope of equivalents to which such claims are entitled. The scope of the disclosure is further qualified as including any possible modification to any of the aspects and/or embodiments disclosed herein which would result in other embodiments, combinations, subcombinations, or the like that would be obvious to those skilled in the art.

The present disclosure is not to be limited to that described herein. Mechanical, electrical, chemical, procedural, and/or other changes can be made without departing from the spirit and scope of the present disclosure. No features shown or described are essential to permit basic operation of the present disclosure unless otherwise indicated.

Small animals, such as dogs and cats, are commonly affected with head and neck cancers, such as brain tumors and nasal tumors, which are treated with external beam radiotherapy. However, for purposes of the present disclosure, it should be appreciated that any types of treatments utilizing radiation therapy, such as for all types of cancers, could be considered part of the disclosure. In general, radiotherapy or radiation therapy is a therapy using ionizing radiation, generally provided as part of cancer treatment to control or kill malignant cells and normally delivered by a linear accelerator. Radiation therapy may be curative in a number of types of cancer if they are localized to one area of the body. As should be appreciated, the use of radiotherapy and radiation therapy should be understood to be used interchangeably herein.

As shown in FIG. 1, aspects and/or embodiments of the present disclosure include an assembly 10 for holding a patient, i.e., a small animal (cat or dog), during radiotherapy treatment. The system 10 includes a table 12 for holding the patient. On the table 12 is a frame 14. The frame 14 may be a human positioning device (Standard U-Frame for radiotherapy by CIVCO but will also work with u-frames from other manufacturers e.g., Klarity). Also shown in the figure is a ruler 13 along the edges of the table.

The frame 14 is a positioning surface. Positioning devices are necessary to immobilize the head and neck for reproducible radiotherapy treatments and computed tomography simulation. The positioning device 14 can be operatively connected, such as mechanical fasteners or other temporary connections, to the table 12 to aid in knowing the position of the patient for directed radiotherapy treatment.

Figure 2:
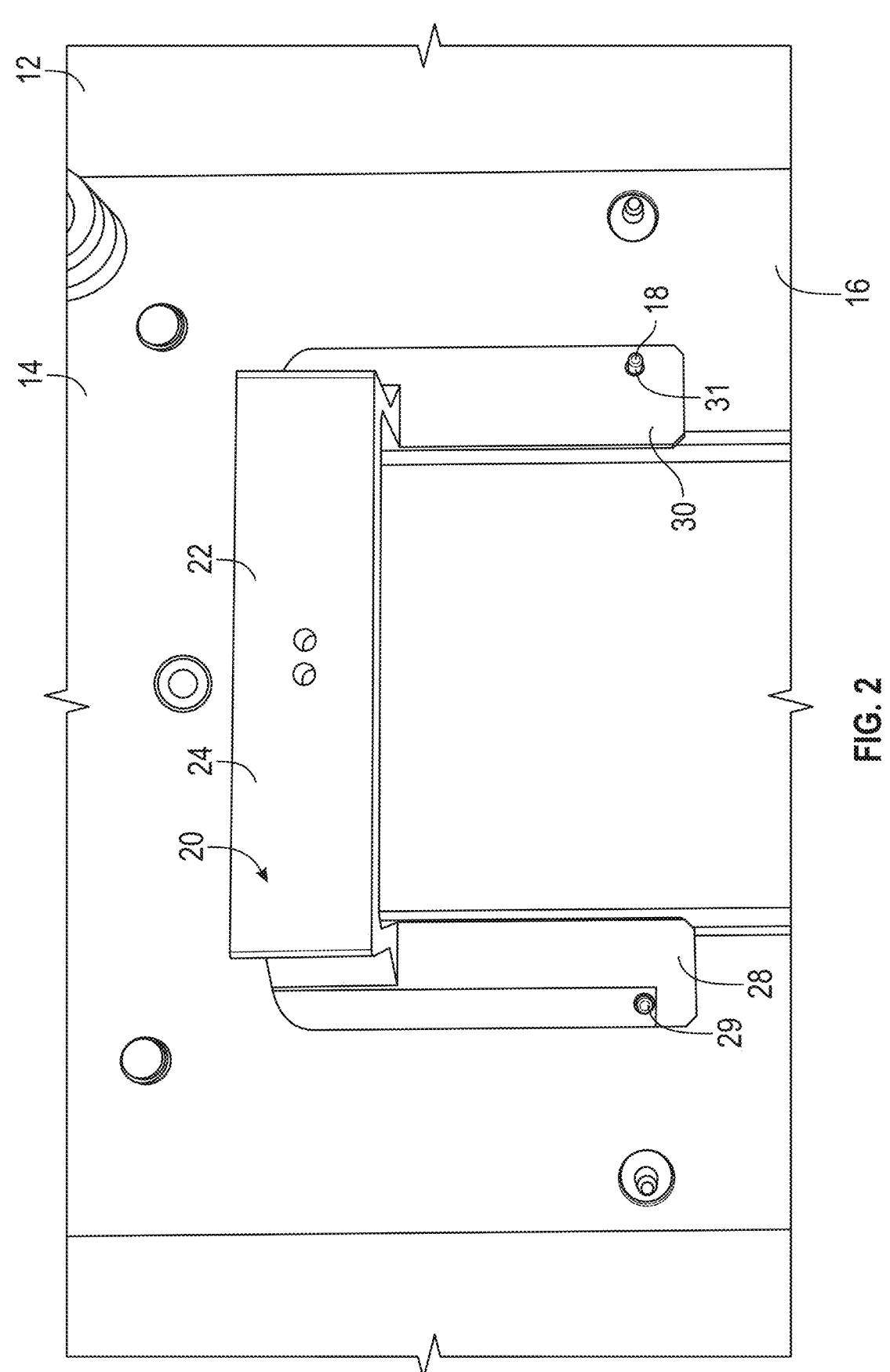
FIG. 2 is a top view of a portion of the system of FIG. 1.
Figure 3:
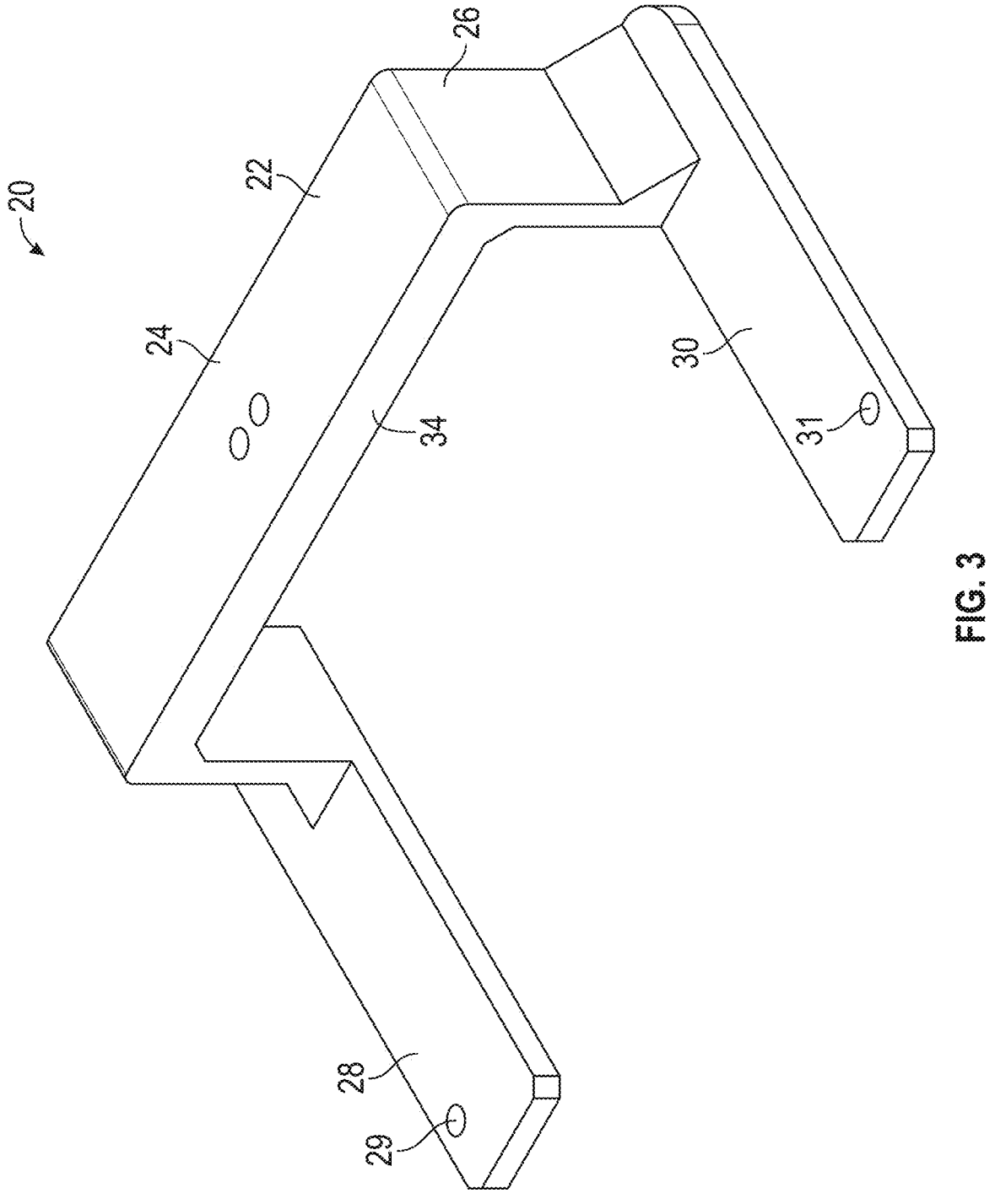
FIG. 3 is a perspective view of a device for use in radiotherapy treatment for small animals, such as dogs and cats.
Figure 4:
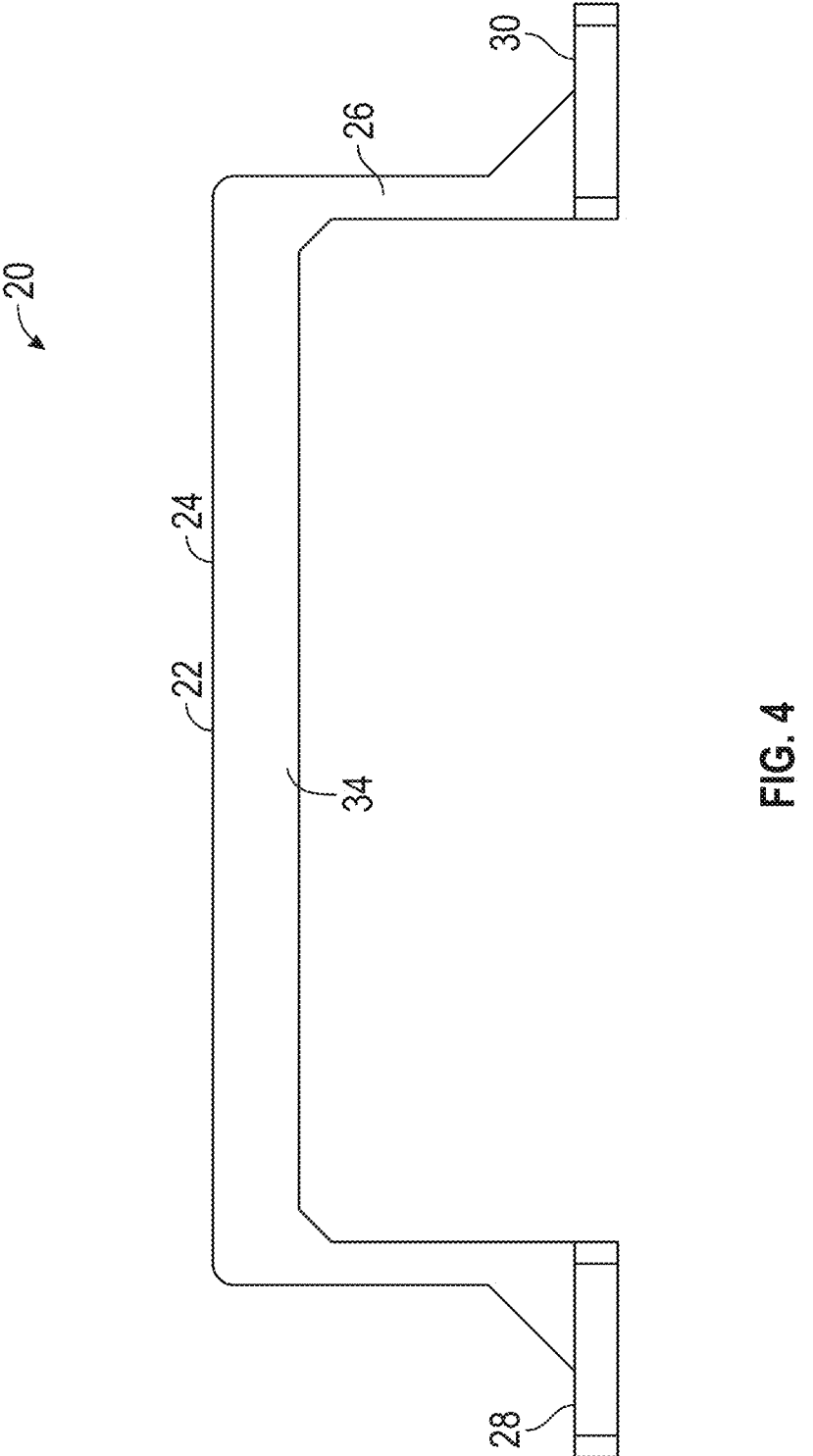
FIG. 4 is a front elevation view of the device of FIG. 3.
Figure 5:
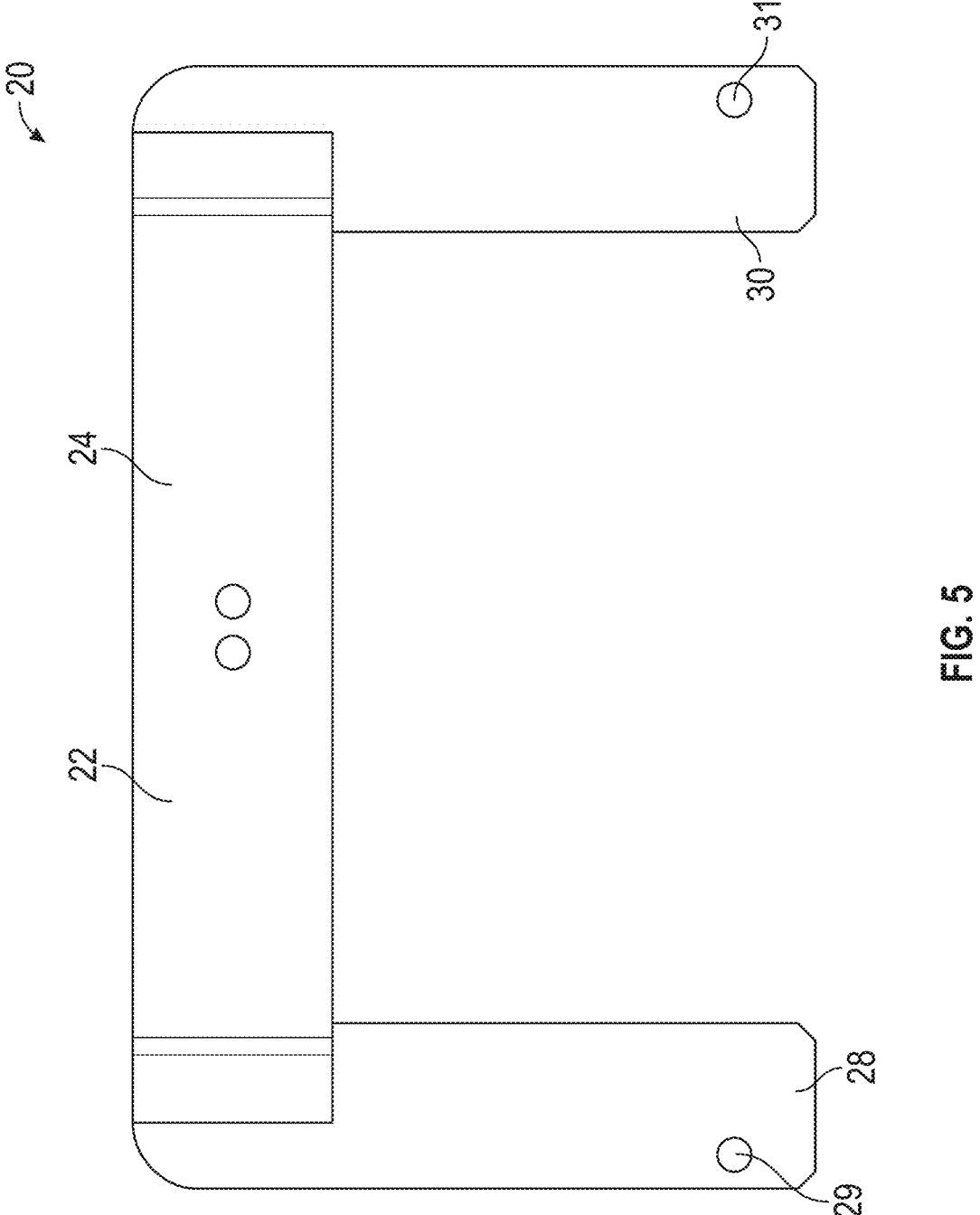
FIG. 5 is a top plan view of the device of FIG. 3.
Figure 6:
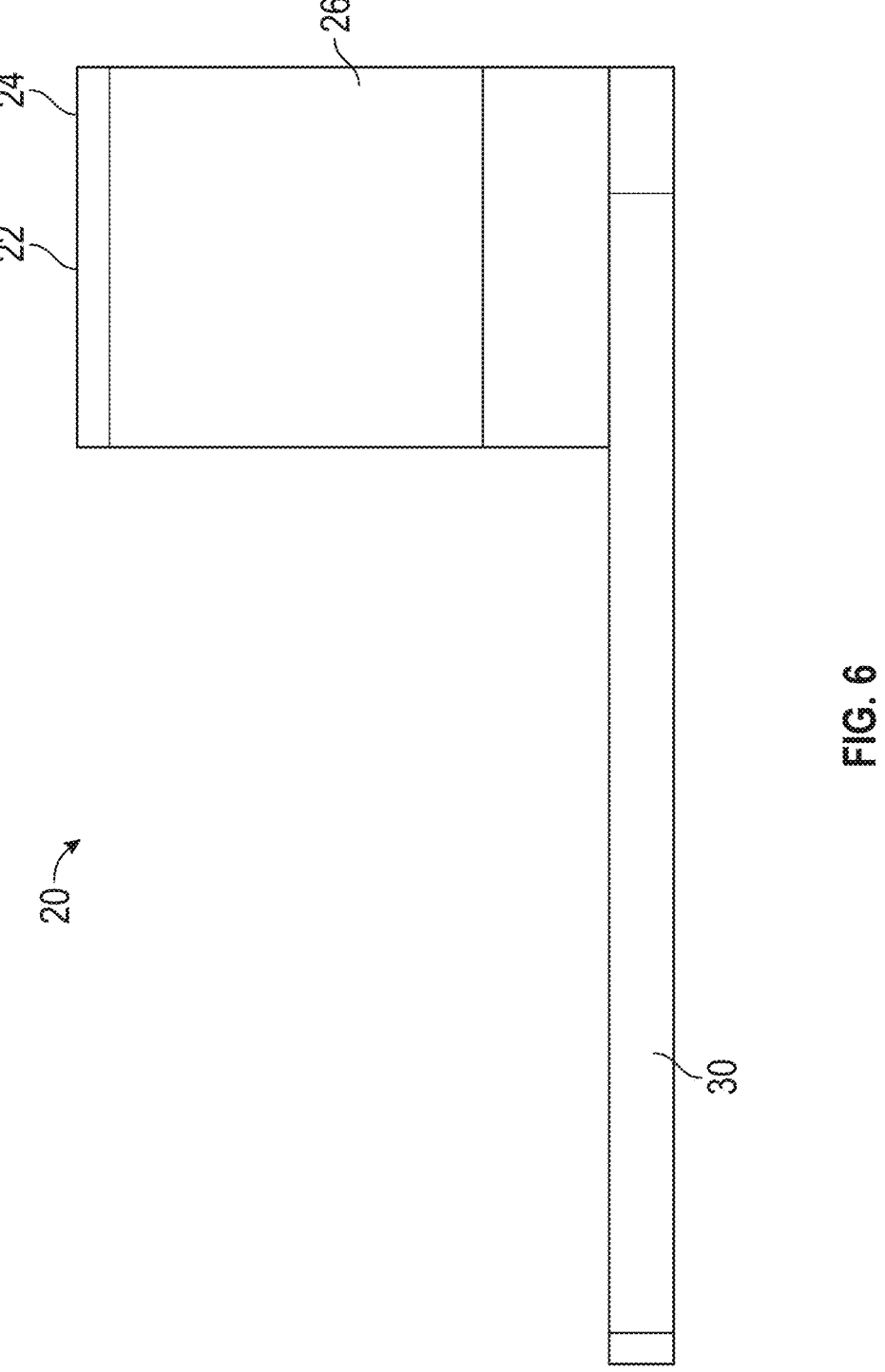
FIG. 6 is a side elevation view of the device of FIG. 3.
Figure 7:
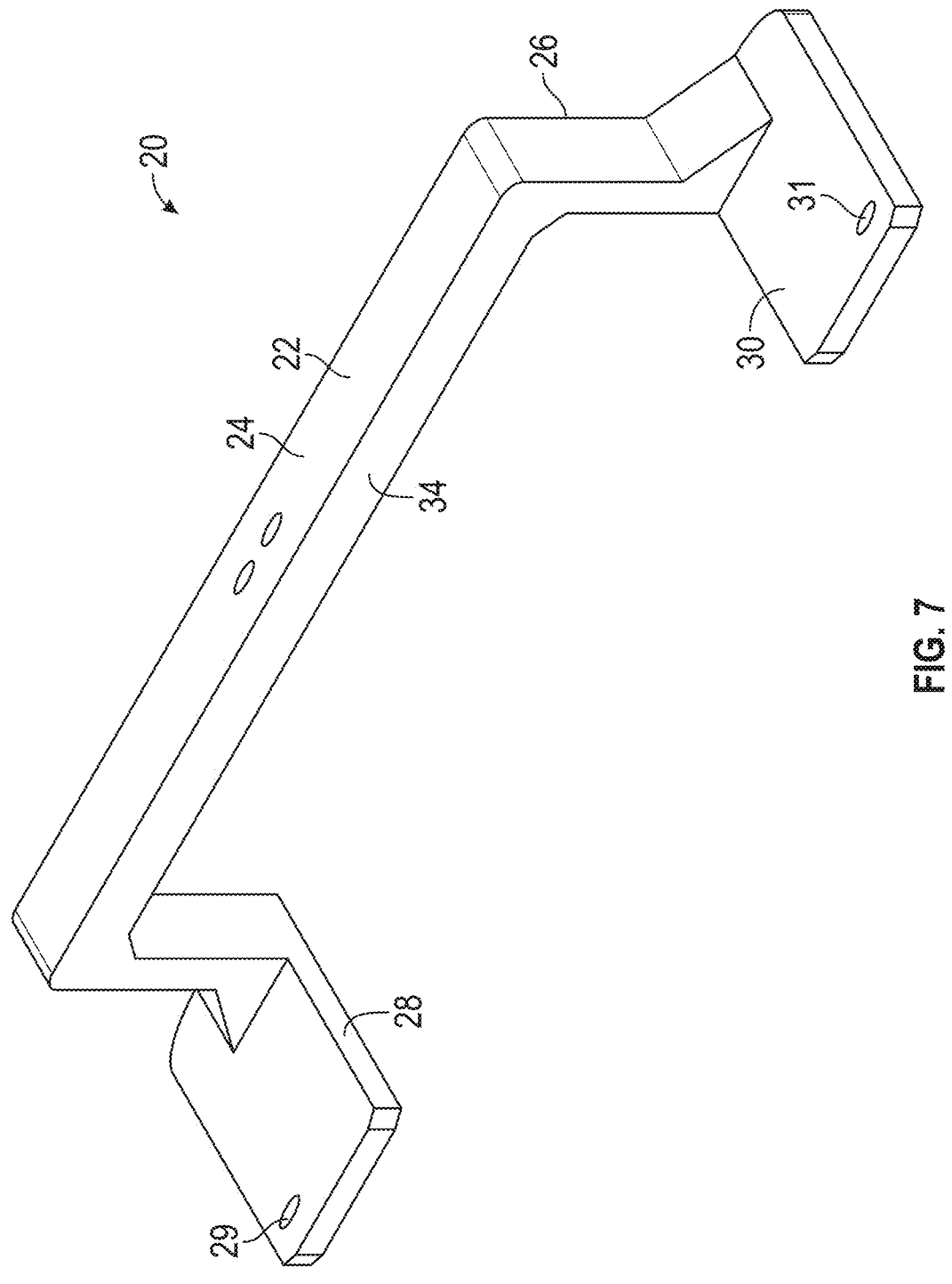
FIG. 7 is a perspective view showing a device such as shown in FIG. 3, but with different dimensions.
Figure 8:
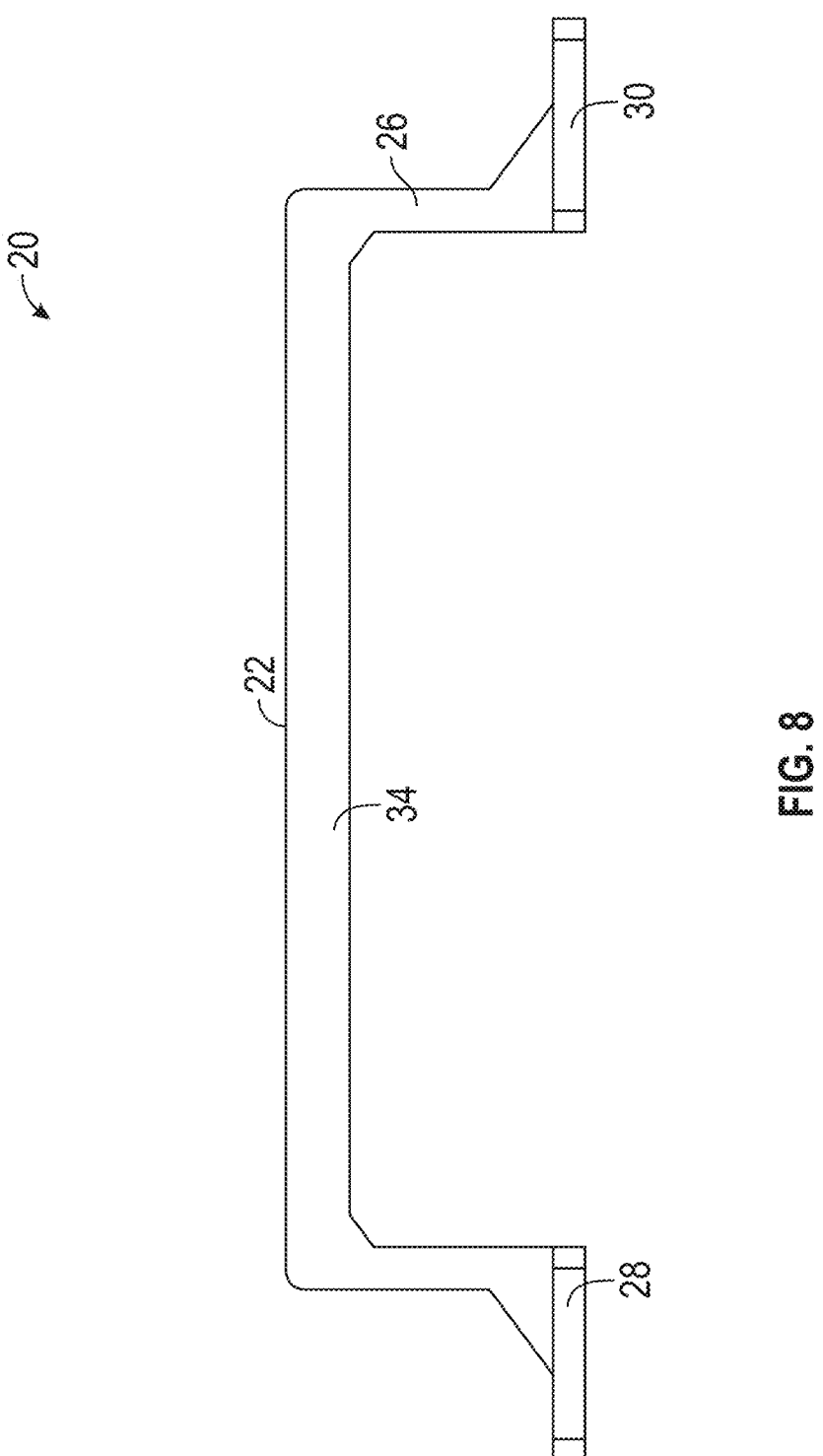
FIG. 8 is a front elevation view of the device of FIG. 7.
Figure 9:
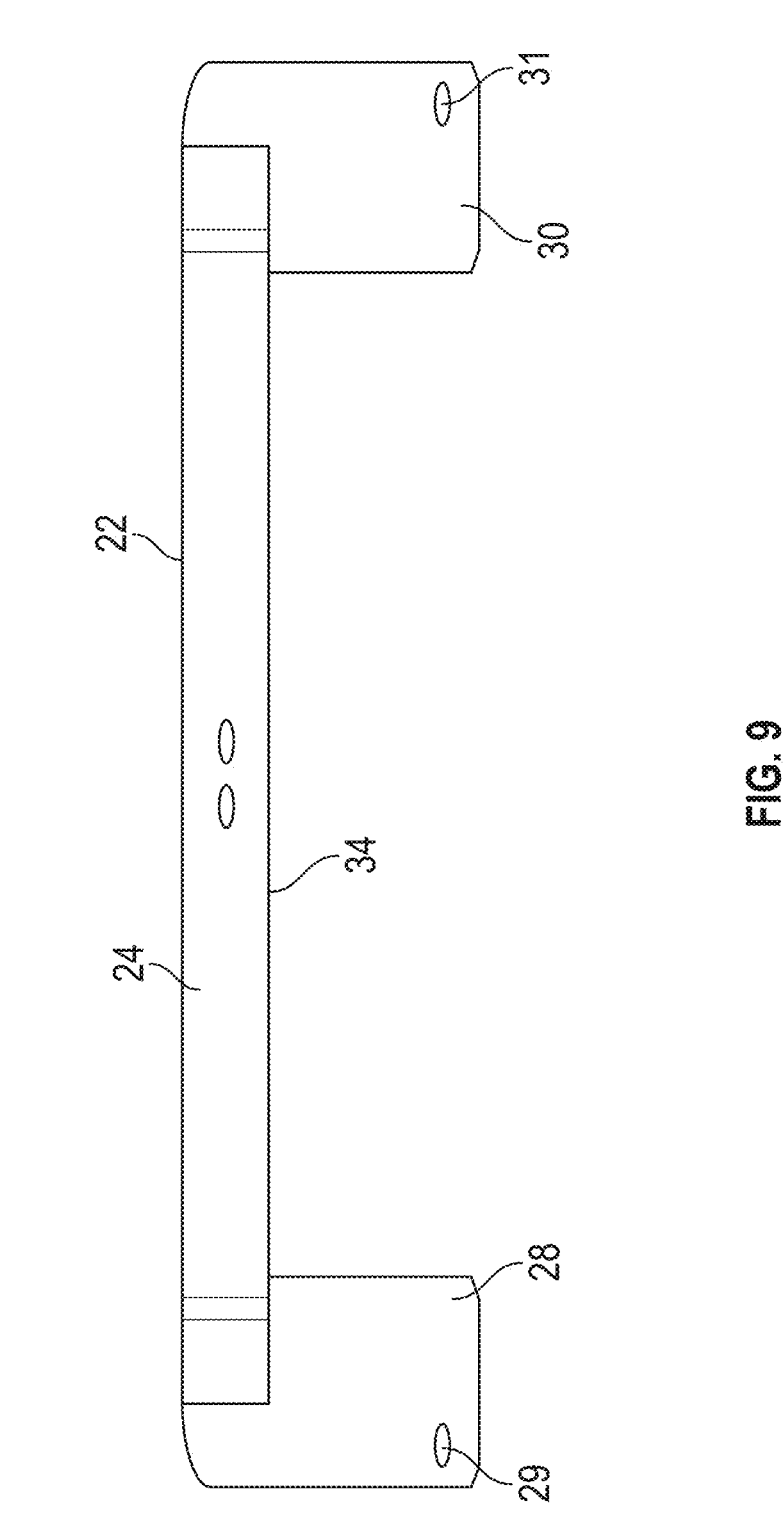
FIG. 9 is a top plan view of the device of FIG. 7.
Figure 10:
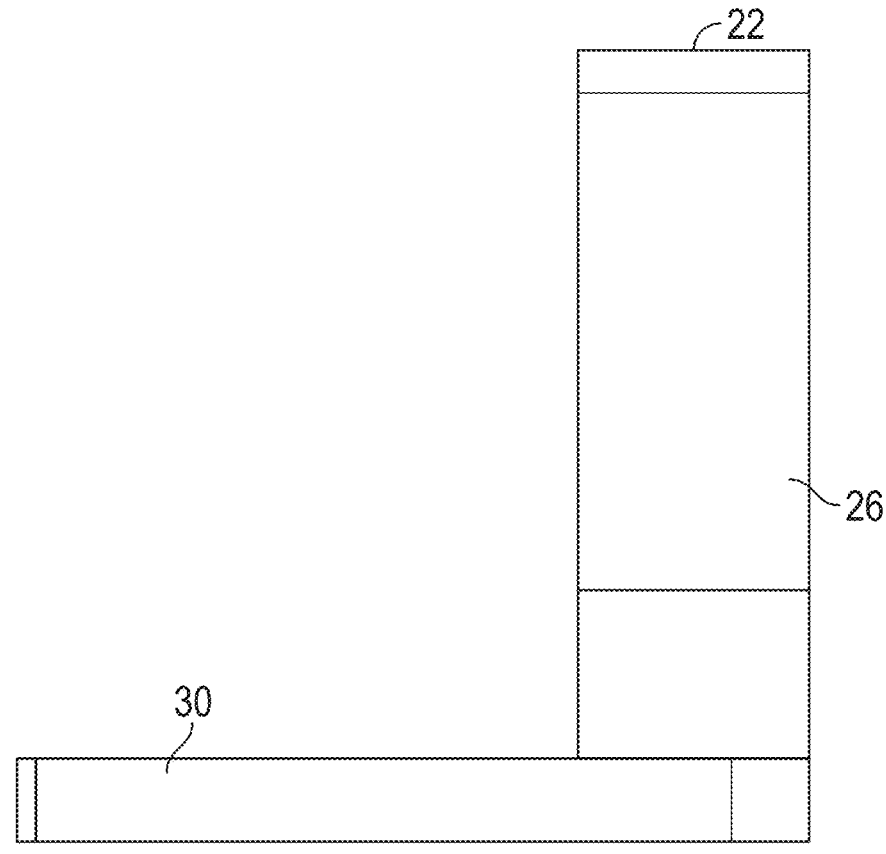
FIG. 10 is a side elevation view of the device of FIG. 7.

To further aid in the positioning of a small animal patient for such treatment, a positioning device 20 is shown in FIGS. 1 and 2. The positioning device 20 may also be referred to as a plate. The frame 14 includes a surface 16 and upwardly extending indexing tabs 18 from the frame. As the tabs 18 are welded or otherwise fixed in location on the frame 14, positioning the frame 14 relative to the table 12 will also fix the location of the tabs 18. As will be understood, the tabs 18 can be used to position the device 20 relative to the frame 14, which will further ensure the location of the patient undergoing the radiotherapy treatment.

As shown in FIGS. 3-6, a device 20 is shown. The device 20 includes a raised platform 22 spanning between two support legs 26. The raised platform includes a surface 24 that is shown to be substantially rectangular in shape. However, this should not be limiting on the disclosure, and other shapes, whether symmetric or not, may be utilized. As will be understood, the raised platform 22 is used to position the mouth of a patient undergoing radiotherapy treatment.

The height of the platform 22, and thus the height of the support legs 26 can vary and is not to be limiting on the disclosure. The same goes for the width and/or length of the platform. The width is considered the distance between a front face 34 and a rear face 32, and the length is the distance between the two support legs 26. Even further, the thickness of platform (i.e., the distance between the top and bottom of the platform) can also be varied to accommodate different animal types and breeds.

The support legs 26 are shown to be approximately transverse to the length of the platform 22 in the figures, but it should be appreciated that the legs may be at an angle greater than 90 degrees as well. The support legs may also include portions of greater thickness for additional support.

Extending substantially transverse to the support legs 26 and away from the legs 26 and platform 22 are a first base foot 28 and a second base foot 30. The base feet 28, 30 may be of varying length and width, which may be at least partially determinative on the size of the animal supported by the device 20. As shown in the figures, the first base foot 28 includes a first indexing aperture 29 and the second base foot 30 includes a second indexing aperture 31. The indexing apertures 29, 31 are positioned through the base feet a distance that corresponds to the indexing tabs 18 of the frame. In this manner, the device can be temporarily positioned relative to the frame 14 at a known location.

The device 20 can be a one-piece, integral unit, or can be comprised of singular components connected to one another. For example, according to at least some aspects and/or embodiments, the device 20 is a singular unit that is made by additive manufacturing (e.g., 3D printing) and can be made of a plastic epoxy, such as acrylonitrile butadiene styrene (ABS), or other thermoplastic.

As noted, the device 20 can take many different configurations, such as variations in the size and/or shape of many of the portions of the device. At least one different configuration is shown in FIGS. 7-10. As shown in the figures, a device 20 includes the same basic components, which includes a raised platform 22 with an upper surface 22, front face 34, and rear face 32. The raised platform 22 spans a length between two opposite support legs 26, which extend generally downward from the platform 22, such as at approximately 90-degrees therefrom.

At distal ends of the support legs 26 are a first foot 28 and a second foot 30. The feet 28, 30 extend generally transverse to the support legs 26, such as away from the front face 34 of the raised platform 22. The feet also include indexing apertures 29, 31, similarly to that previously shown and described. Again, the indexing apertures are positioned in the feet and spaced from one another to correspond to indexing tabs 18 of a standard U-frame positioning device for use in radiotherapy treatment.

Also similar to that shown and described, the device shown in FIGS. 7-10 can comprise a unitary piece, such as being made by 3D printing or other additive manufacturing process. In addition, it should also be appreciated that any device of any configuration can be made from other types of manufacturing, such as, but not limited to, molding, shaping, or the like. The exact type of manufacture should not be limiting on the disclosure as a whole, and may be determined by material type, size, needed structural integrity, and any other factor.

As noted in the figures, there are numerous differences in the sizes of the device shown in FIGS. 3-6 and FIGS. 7-10. For example, the length, width, and thickness of the raised platform are different. Still further, the dimensions of the feet are different between the sets of figures. However, the locations of the indexing apertures, such as the distance therebetween, may be the same to account for the common indexing frame 14 used with the device.

Figure 11:
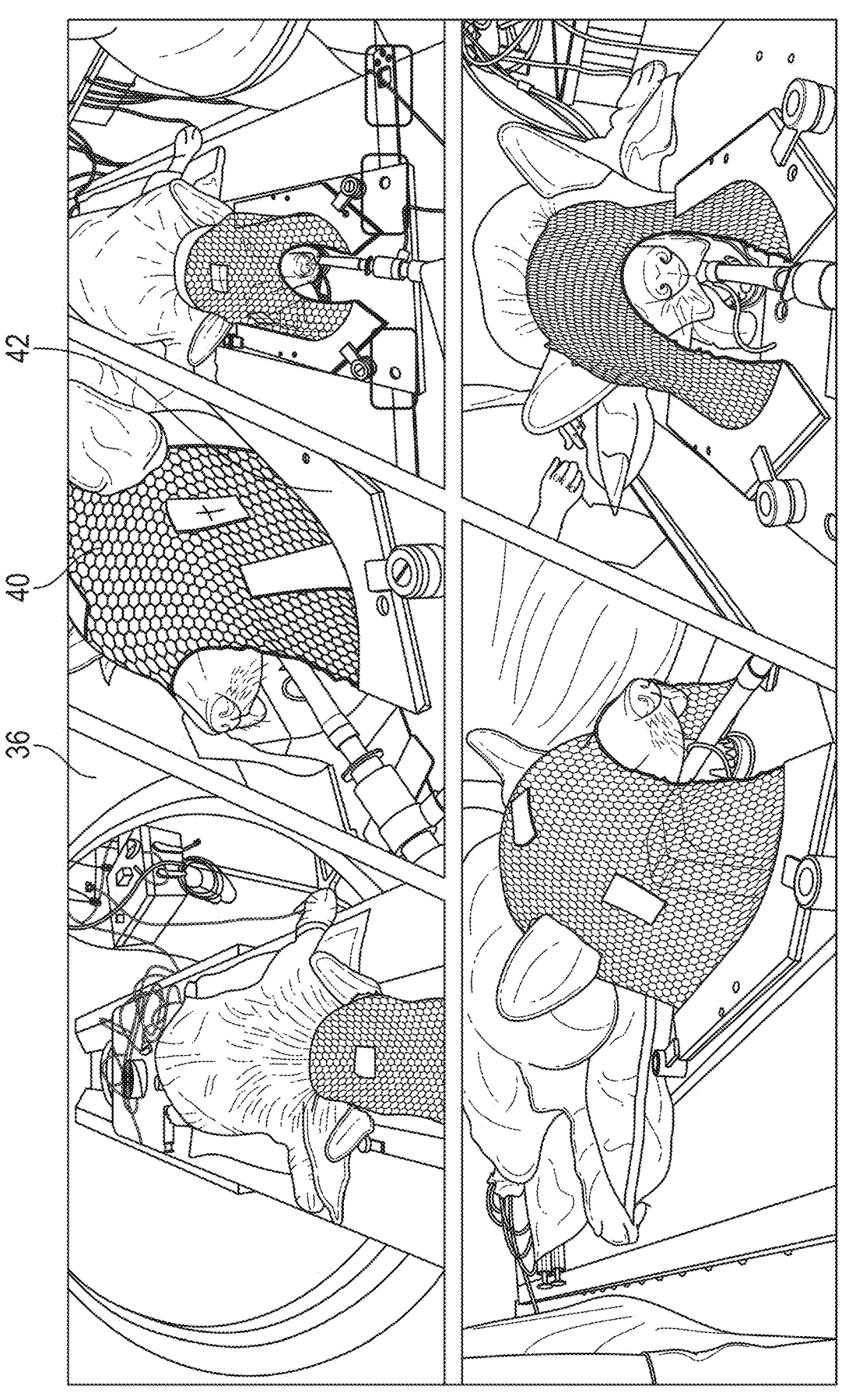
FIG. 11 shows various views of an animal prepped for radiotherapy using systems and/or devices of the present disclosure.

FIG. 11 shows an example use of the system 10 including a device 20 as shown and described herein. As shown in the upper right photo of FIG. 11, the U-Frame 14 is positionable on a human table via indexing and measuring indicia. However, while this positions the U-frame relative to the table, there are still issues with ensuring that the animal patient is reproducibly positioned relative to the U-Frame 14. Therefore, the plate device 20 is indexed to the inner pins/tabs 18 of the commercially available U-Frame 14 and the patient (i.e., animal) is positioned in sternal recumbency under general anesthesia. The upper jaw (maxilla) is placed on the top bridge portion (raised platform 22) of the device 20 and commercially available dental epoxy is used to make a reproducible mold of the upper jaw that is used for subsequent radiation therapy treatments to position the patient. Commercially available thermoplastic material is then applied to the patient's head to immobilize the head and neck rigidly and reproducibly for radiation therapy. The thermoplastic material is shown as a mesh material 40 and is used to further hold the patient in place during radiotherapy. The mesh material 40 may be held in place by holders 42 to allow for a tight positioning of the mesh.

A breathing apparatus connected to an anesthesia machine is shown to be placed in the patient to aid in breathing and maintain immobilization during treatment. The use of the raised platform 22 of the device aids the breathing apparatus by supporting the upper jaw so that the patient does not close their mouth on the breathing apparatus during treatment, which could result in patient death.

Additional elements shown in the figure include a pillow or padded member under the body of the patient during treatment.

As noted, because the table, frame, and device are all indexed to one another, the operator of a radiotherapy device 36, such as shown in FIG. 11, can more confidently know the exact position of the patient to provide the directed treatment to the area needed (i.e., the area of cancer). This is in part due to the ruler 13 on the table and the known location of the device 20 and patient positioned thereon. The known location is important to best treat the area of cancer while avoiding inadvertent treatment of normal tissues with radiotherapy.

Figure 12:
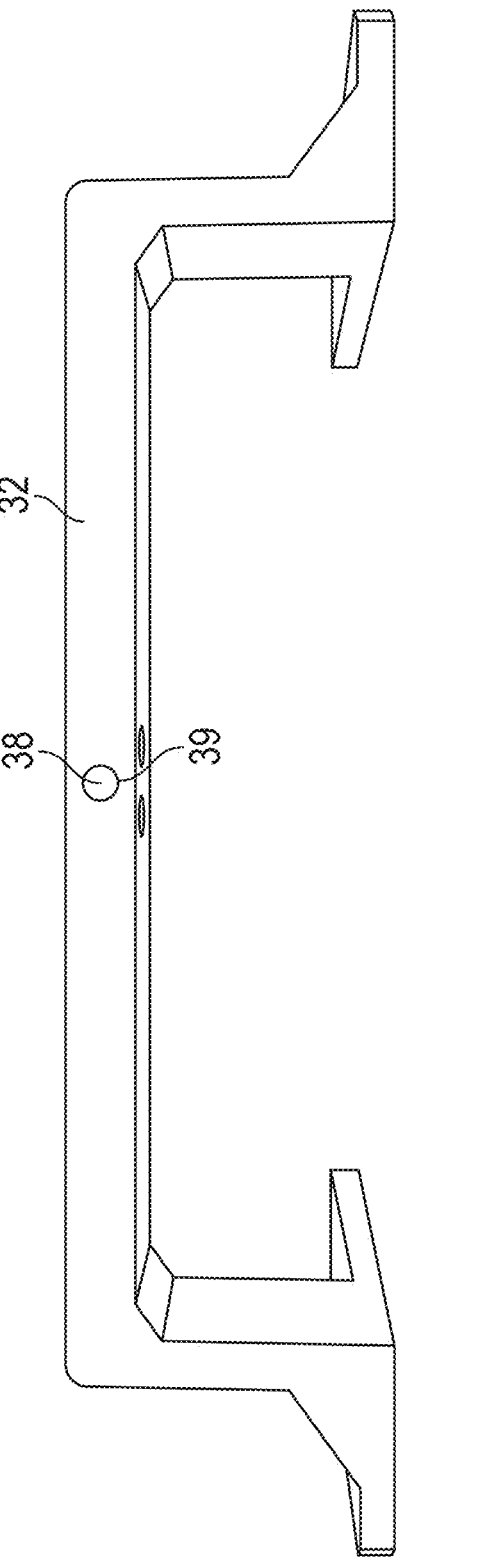
FIG. 12 is another view of a device for use in radiotherapy showing additional aspects of the present disclosure.

FIG. 12 shows yet additional aspects and/or embodiments of the present disclosure. The circle shown on the rear face 32 of the device 20 shown in FIG. 12 could be a plug to put a dosimeter (radiation measurement device called a diode) in the device. This would allow a user to measure the radiation delivered to the roof of the patient's mouth (hard palate) while radiation is administered. It may be useful to measure the radiation dose delivered to the roof of the mouth of a patient because the radiation treatment planning system does a poor job at estimating the dose from the surface of the patient. Sometimes the tumor is right over the roof of the mouth, and we could cause side effects such as a fistula or hole in the roof of the mouth if the radiation dose is too high. The use of such a dosimeter would enable a user to monitor the amount of radiation while treating and integrates the positional device with equipment that is designed to measure the radiation dose in the patient.

While the plug/dosimeter 38, 39 is shown to be positioned at the rear face 32 of the raised platform 22 of the device 20, it should be appreciated that this could be located generally anywhere on or in the device to be able to measure the amount of radiation used during treatment. Such a dosimeter could also include an indicator, such as a visual or audio indicator to alert the operators if the amount of radiation registers above a set threshold.

Therefore, a device that improves radiotherapy treatment for animals, such as small animals, has been shown and described. Such a device provides numerous improvements and/or advantages over the art, which has been shown and described herein. It should be appreciated that obvious changes to that shown and/or described should be considered to be covered by the present disclosure. In addition, the present disclosure appreciates changes to the figures shown, including potential combinations from the figures that are not expressly shown or described.

The invention claimed is:

1. A device for use in radiotherapy treatment of animals, comprising:
   a raised platform;
   first and second feet extending substantially transverse to the raised platform;
   wherein the first and second feet each include at least one indexing aperture that is used to align the device during the radiotherapy treatment, said indexing apertures extending through the feet.

2. The device of claim 1, further comprising an epoxy on the raised platform that is configured to be moldable to an upper jaw portion of the animal undergoing radiotherapy treatment.

3. The device of claim 1, wherein an indexing aperture on the first foot is positioned at the same lateral position as an indexing aperture on the second foot.

4. The device of claim 1, wherein an indexing aperture on the first foot and an indexing aperture on the second foot are distanced the same distance from the raised platform.

5. The device of claim 1, wherein the raised platform comprises a rectangular-shape with support legs extending downward from the rectangular-shaped platform.

6. The device of claim 5, wherein the first and second feet extend away from the support legs of the raised platform.

7. The device of claim 1, further comprising a dosimeter positioned at the raised platform.

8. The device of claim 7, wherein the dosimeter is positioned in a plug in the raised platform.

9. The device of claim 8, wherein the plug is positioned at a rear face of the raised platform.

10. An assembly, comprising:

a radiotherapy positioning frame comprising a surface and a plurality of indexing tabs extending generally upward from the surface; and a radiotherapy positioning device comprising a raised platform and first and second feet extending substantially transverse to the raised platform, wherein the first and second feet each include at least one indexing aperture that is used to align the radiotherapy device relative to the radiotherapy positioning frame via engagement between the indexing tabs and the indexing apertures.

11. The assembly of claim 10, further comprising a thermoplastic material operatively engageable with the frame and/or device to hold an animal in place during radiotherapy treatment.

12. The assembly of claim 10, wherein an indexing aperture on the first foot is positioned at the same lateral position as an indexing aperture on the second foot.

13. The assembly of claim 10, wherein an indexing aperture on the first foot and an indexing aperture on the second foot are distanced the same distance from the raised platform.

14. The assembly of claim 10, wherein the raised platform comprises a rectangular-shape with support legs extending downward from the rectangular-shaped platform.

15. The assembly of claim 14, wherein the first and second feet extend away from the support legs of the raised platform.

16. The assembly of claim 10, further comprising a dosimeter positioned at the raised platform.

17. The assembly of claim 16, wherein the dosimeter is positioned in a plug in the raised platform.

18. A device for use in radiotherapy treatment of animals, comprising:

a raised platform;

first and second feet extending substantially transverse to the raised platform;

wherein the first and second feet each include at least one indexing aperture that is used to align the device during the radiotherapy treatment, said indexing apertures extending through the feet;

wherein the raised platform comprises a rectangular-shape with support legs extending downward from the rectangular-shaped platform.

19. The device of claim 18, wherein the first and second feet extend away from the support legs of the raised platform.

20. The device of claim 18, further comprising a dosimeter positioned at the raised platform.

\* \* \* \* \*